US007713207B2

(12) United States Patent
Vilkomerson

(10) Patent No.: US 7,713,207 B2
(45) Date of Patent: May 11, 2010

(54) ULTRASONIC APPARATUS AND METHOD FOR GENERATING AUDIO SIGNALS USING DOPPLER

(75) Inventor: David Vilkomerson, Princeton, NJ (US)

(73) Assignee: DVX, LLC, Princeton, NJ (US)

( * ) Notice: Subject to any disclaimer, the term of this patent is extended or adjusted under 35 U.S.C. 154(b) by 693 days.

(21) Appl. No.: 11/593,887

(22) Filed: Nov. 7, 2006

(65) Prior Publication Data
US 2007/0167783 A1    Jul. 19, 2007

Related U.S. Application Data

(60) Provisional application No. 60/734,354, filed on Nov. 7, 2005.

(51) Int. Cl.
*A61B 8/00* (2006.01)
(52) U.S. Cl. ...................... 600/443; 600/323
(58) Field of Classification Search ............... 600/455, 600/323
See application file for complete search history.

(56) References Cited

U.S. PATENT DOCUMENTS 4,607,642 A * 8/1986 Powers ................ 600/455
4,770,184 A * 9/1988 Greene et al. ............ 600/454
5,103,827 A * 4/1992 Smith .................... 600/454
5,409,010 A * 4/1995 Beach et al. ............. 600/455
5,846,203 A * 12/1998 Koo et al. ............... 600/454
6,468,219 B1 * 10/2002 Njemanze ............... 600/454
6,514,208 B1 * 2/2003 Cancio et al. ............ 600/454

OTHER PUBLICATIONS

"An Instrument for Screening for Carotid Disease", D. Vilkomerson and T. Chilipka in the Proceedings of the 2005 IEEE International Ultrasound Symposium.
"Easy-to-Use Blood Velocity Measurement Instruments", D. Vilkomerson and T. Chilipka, in the Proceedings of Medical Imaging 2003, W. Walker and M. Insana Eds., Proceedings of SPIE, vol. 5035; SPIE, Bellingham, WA 2003.

* cited by examiner

*Primary Examiner*—Long V Le
*Assistant Examiner*—Saurel J Selkin
(74) *Attorney, Agent, or Firm*—Plevy & Keene LLP

(57) ABSTRACT

An ultrasound system provides Doppler spectral data indicative of a monitored moving fluid. The spectral data is analyzed according to the level of power in specified Doppler frequency ranges. Audio signals indicative of each analyzed range are generated to enable a user to audibly determine said range is in order to detect a certain condition manifested by said fluid motion.

20 Claims, 5 Drawing Sheets

Carotid Screening System with
Synthetic Doppler Audio

Conventional Doppler

Carotid Screening System

Carotid Screening System with
Synthetic Doppler Audio

ULTRASONIC APPARATUS AND METHOD FOR GENERATING AUDIO SIGNALS USING DOPPLER

CLAIM FOR PRIORITY

This application claims priority under 35 USC 119(e) to U.S. Provisional Patent Application No. 60/734,354, filed Nov. 7, 2005, entitled "Doppler Instruments By Synthesizing Audio Signals" the entire disclosure of which is incorporated by reference herein.

FIELD OF INVENTION

This invention relates to Doppler medical devices generally, and more particularly to instruments that use Doppler-derived audio signals for guidance and diagnosis.

BACKGROUND OF THE INVENTION

A widely used method of measuring blood velocity uses the Doppler shift in ultrasound backscattered by red blood cells in moving blood. Ultrasound frequencies that can penetrate the body, for example frequencies in the range of 1-10 Megahertz (MHz), are Doppler-shifted by frequencies that fall in the human range of hearing when they strike blood velocities found in the body, such velocities ranging from about 10 centimeters/second to 5 meters/second. Therefore, when backscattered ultrasound is coherently detected with the transmitted frequency, the Doppler shifted signal, which is proportional to the blood velocity, is audible. This led to the early use of Doppler in medical diagnoses.

With the development of spectrum analysis to quantitate the Doppler shifts, the importance of audible Doppler diminished, as the blood velocity can be found directly from the spectrum.

The audible Doppler signal is still used to find blood vessels and to check for their patency. In addition, there exists a new class of screening ultrasound systems, for example "An Instrument for Screening for Carotid Disease", in the "Proceedings of the 2005 IEEE International Ultrasound Symposium" (incorporated herein by reference) that utilizes Doppler-audible signals to guide an inexperienced operator in moving the ultrasound probe over the carotid arteries. To find the diseased portions of the carotid system, the operator must detect what can be a faint, high-frequency whisper, indicating the high velocity caused by a stenosis, among other, louder signals produced by normal portions of the carotid arteries.

While previous Doppler instruments have used filters to help in that regard, it has been a challenging situation for inexperienced operators; for screening to succeed, many inexperienced operators will be required. Interpreting the audible Doppler signal is an obstacle to such screening systems.

Alternative methods and apparatus that facilitate detection of Doppler audio signals from diseased vessels, particularly by inexperienced operators, is desired.

SUMMARY OF THE INVENTION

In the same way that pathologists "stain" tissue structures to make it easier to detect diseased tissue, real-time Doppler spectra is used to generate synthetic Doppler audio to make it easier to recognize Doppler signals from diseased vessels or other abnormal flow conditions. The apparatus and method disclosed here produces synthesized Doppler signals for better detection of the condition of the cardiovascular system.

An ultrasound system provides Doppler spectral data indicative of a monitored moving fluid. The spectral data is analyzed according to the level of power in specified Doppler frequency ranges. Audio signals indicative of each analyzed range are generated to enable a user to audibly determine said range is in order to detect a certain condition manifested by said fluid motion.

In one aspect of the invention, an apparatus for generating selected audio signals to aid in the detection of a certain condition of a moving fluid comprises an ultrasound system for measuring the velocity of a fluid and operative to provide spectral data indicative of the velocity, a processor responsive to the spectral data and operative to analyze at least one power spectrum indicative of a fluid velocity in a given range to provide an output signal, and a generator responsive to the output signal to provide a unique audio signal according to the given range.

In another aspect of the present invention, a method for generating selected audio signals to aid in the detection of certain conditions, comprises the steps of generating an ultrasonic signal, causing the signal to impinge upon a moving fluid to provide Doppler spectral data according to the velocity of the fluid, analyzing the spectral data to determine the level of power at different Doppler frequency ranges in the spectral data, and producing a unique audio signal for each Doppler frequency range to enable an operator to respond to the audio signal to determine a certain condition.

DETAILED DESCRIPTION OF THE INVENTION

In accordance with aspects of the present invention, there is provided exemplary method and apparatus for generating synthetic audio for screening a carotid system. These examples serve to teach those skilled in the art how this method and apparatus can be used for other types of Doppler systems that utilize audible Doppler signals.

Figure 1:
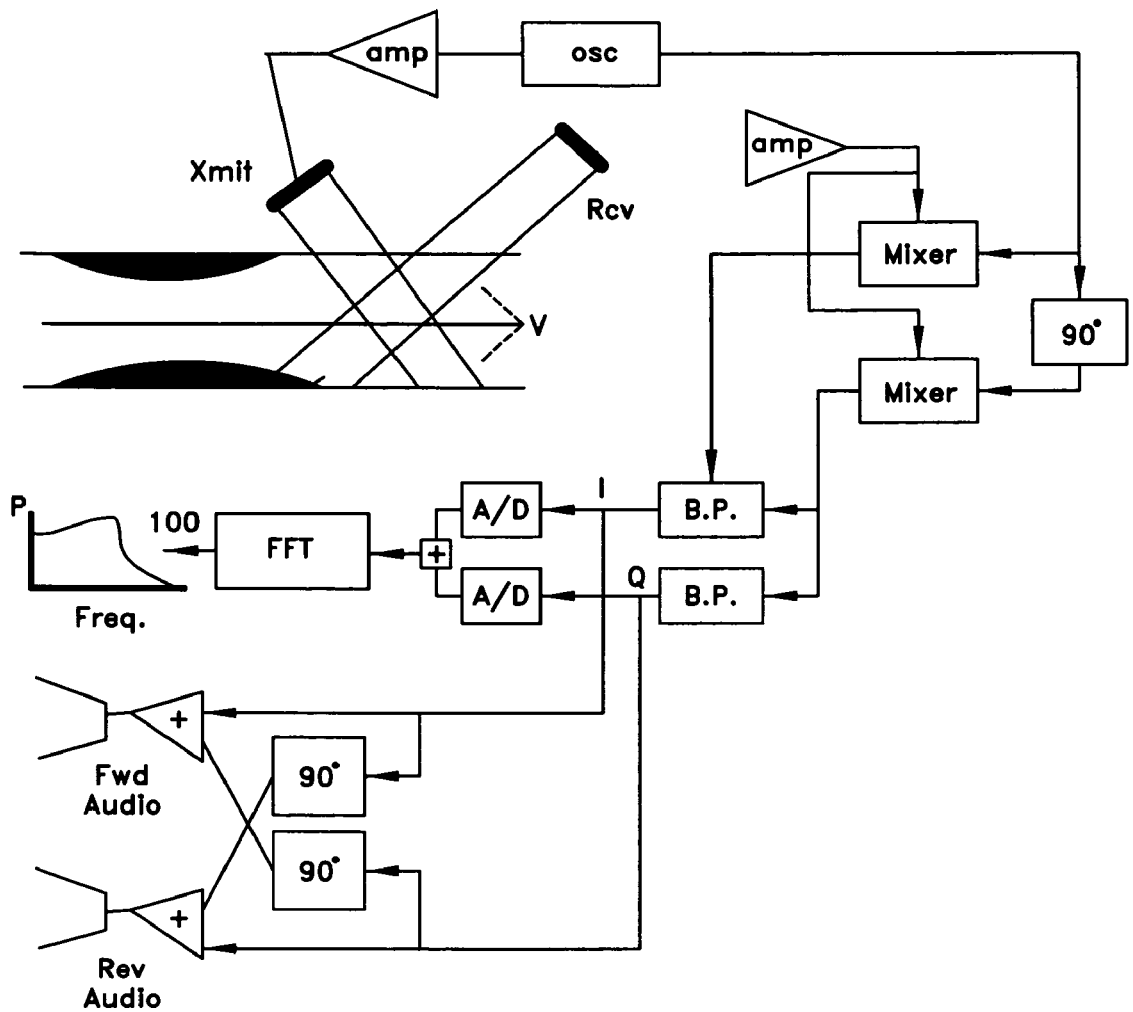
FIG. 1 is a schematic representation of a conventional generalized Doppler system, showing how the usual Doppler audible signal is derived.

For reference, FIG. 1 is a schematic representation of a conventional system that generates audible Doppler signals (for example, as described in "Doppler Ultrasound", 2$^{nd}$ Edition, by Evans and McDicken, John Wiley & Sons, Chichester, 2000, Chapter 6). As shown, the system measures the velocity V of blood after it has passed through a stenosis, a common application of Doppler instruments. The electronic signal produced by backscattered ultrasound striking a receiver, for example of piezoelectric material, is amplified and multiplied by two signals of equal frequency to the transmitted signal, with one of the signals at a 90° phase shift to the other. The multiplication of the backscattered signal produces a DC component, a double-frequency component, and a component of frequency equal to the difference between the backscattered frequency and the transmitted frequency. A bandpass (B.P.) filter removes the DC and double-frequency signals, and the two quadrature components of the Doppler, known in the literature as I&Q, are produced. Either of these components can be used to produce an audio signal, or as is well-known (see, for example, Evans et al op cit, pg. 108) with phase-shifting and summing as shown in FIG. 1, the frequencies arising only from blood moving toward the transducer (forward audio) can be separated from the signals produced by the blood moving away (reverse audio).

Figure 2:
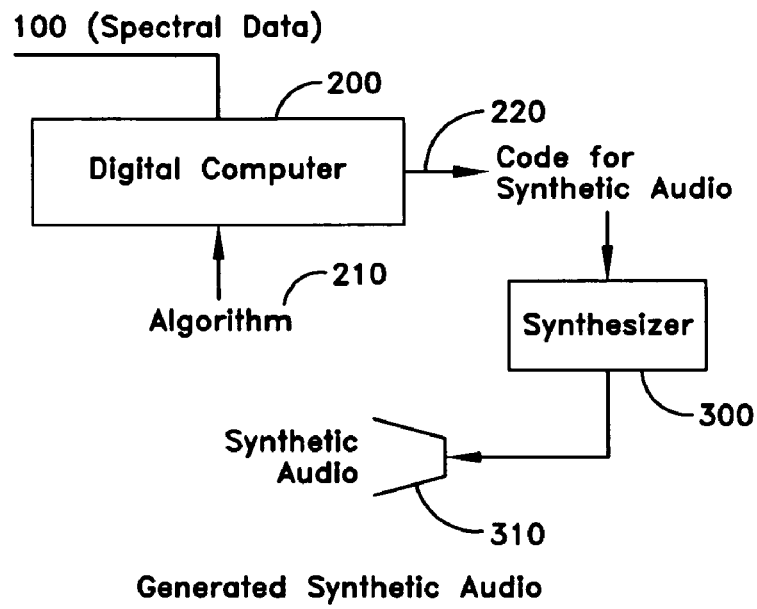
FIG. 2 presents schematically how synthesized Doppler audio signals are derived.

FIG. 2 shows how Synthetic Doppler Audio (SDA) is generated from the spectral data identified in FIG. 1 as 100 and input to processor 200. The FFT spectrum of a particular interval in time, a sequence of digital numbers representing the power at different Doppler frequencies (determined by velocity and angle to the insonating beam), shown in FIG. 1, is analyzed by means of a program 210 (e.g. algorithm) executed by processor 200 that produces digital signals 220 that code for artificial audio signals that are produced by an audio synthesizer 300. The output 310 of audio synthesizer 300 is the synthetic audio signal. FFT stands for Fast Fourier Transform which is well known to those skilled in the art.

Figure 7A:
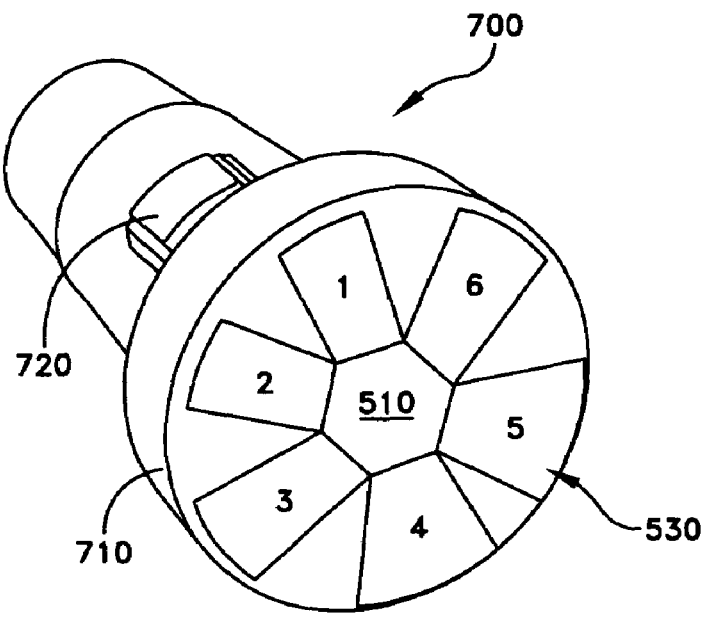
FIG. 7a, 7b show a perspective view and a schematic cross sectional view, respectively, of an exemplary embodiment of a scanning instrument having a scanhead and six receiving transducers surrounding a central transmitter useful in implementing the present invention.
Figure 7B:
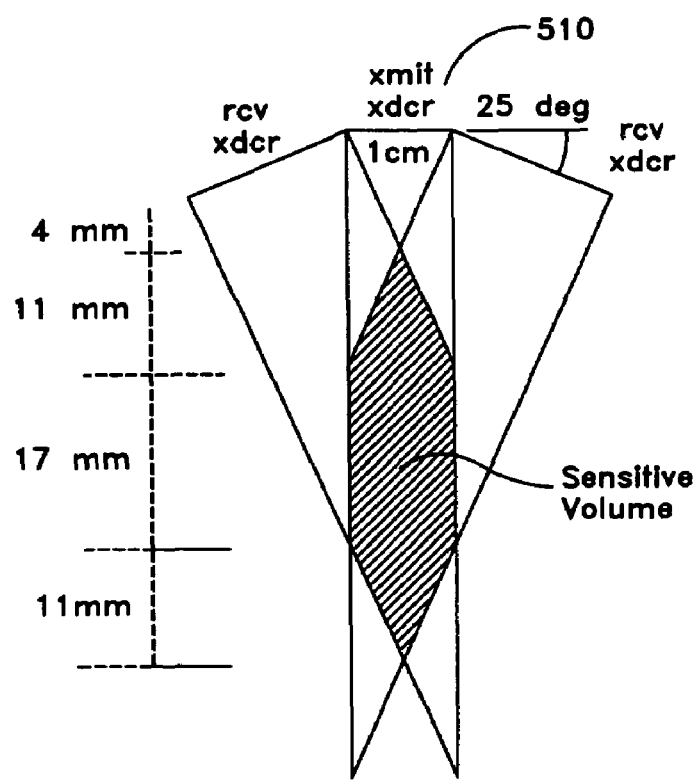

FIG. 7a, 7b show a perspective view and a schematic cross sectional view, respectively, of an exemplary embodiment of a scanning instrument 700 having a scanhead 710 and six receiving transducers 540 surrounding a central transmitter 510 useful in implementing the present invention. As described in the paper "An Instrument for Screening for Carotid Disease", in the Proceedings of the 2005 IEEE International Ultrasound Symposium" (incorporated herein by reference), and still referring to the exemplary embodiment of FIG. 7a-7b, six receiving transducers, typically 10 mm wide by 15 mm in length, surround a central 10-mm diameter transmitter; all operate at 5 MHz resonance frequency f1. As shown in the cross-section of the scanhead, FIG. 7b, the receivers are canted at an angle of 25 degrees, creating a "sensitive volume" where the transmit and receive beams overlap and within which moving blood will produce a Doppler signal in the receivers. This region is 39 mm long, deep enough to reach almost all carotid vessels around the bifurcation, the region where stenoses occur. (As the carotids are 7 mm or less in diameter, the 10 mm sensitive volume allows easy placement of the scanhead.).

The need for six receivers arises from the anatomy of the carotids: rather than being parallel to the skin surface, as many arteries are, after the common carotid bifurcates, the external and internal are frequently at an angle to the skin plane. There will be angles for which the net Doppler shift for three of the receivers can be zero or so low that it is thump-filtered out. By using 6 symmetrically placed transducers, no matter what the angle of the carotid arteries, at least three Doppler shifts can be measured, and from those three Doppler signals, the absolute velocity calculated.

The electronics to determine the Doppler shifts from the six receivers includes conventional CW Doppler signal processing with six pairs of I & Q signals being sampled at 20 KHz and multiplexed into a single 16-bit A/D. Doppler signals from two of the receiving transducers, at the "top" and "bottom" of the transducer are directionally Doppler processed to suppress the jugular flow (which moves in the direction opposite that of the carotid flow) signal; that large signal would otherwise mask the carotid Doppler signal that the operator uses to guide the scanhead. A mark on the scanhead, just visible in FIG. 1 shows the desired orientation, i.e. mark towards the head.)

That audible signal is also is sent to the laptop computer that is used for the display, operator interface, and digital signal processing; a commercially available ActiveX program computes a spectrogram of the audible signal displayed on the screen, further helping to guide the operator.

Figure 3:
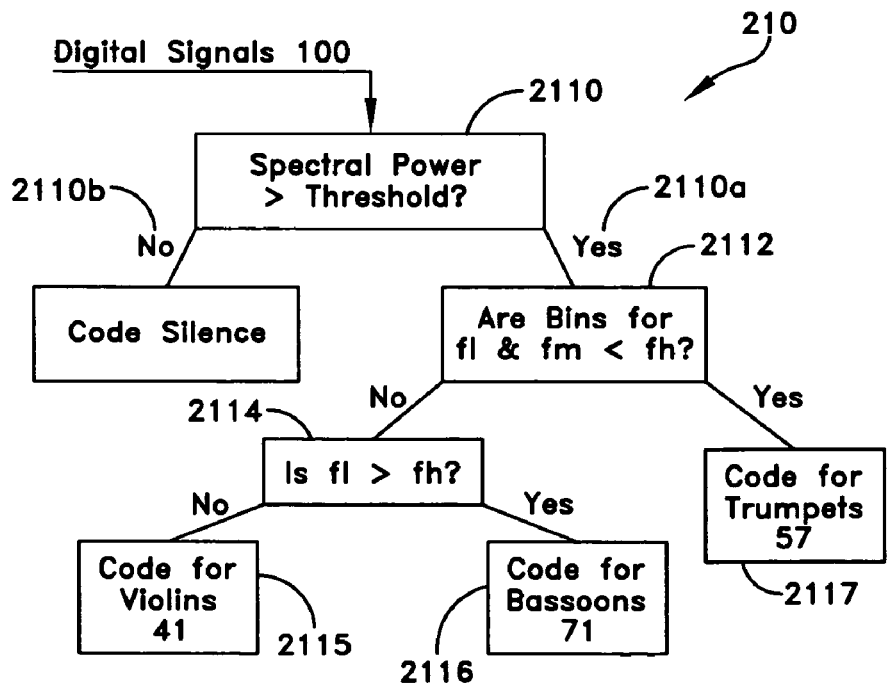
FIG. 3 is a simplified flow-chart of an algorithm indicated in FIG. 2, with indications of an exemplary MIDI (Musical Instrument Digital Interface) code.

FIG. 3 shows a simplified flow-diagram of a program for use in the apparatus in FIG. 2 (and the instrument of FIG. 7). The power spectrum is analyzed (2110) to determine how much signal power is in different parts of the Doppler spectrum, e.g. the sum of the powers in the bins within a certain range of Doppler frequencies. If the spectral power exceeds a given threshold, processing proceeds along the path illustrated by 2110a. Otherwise, processing proceeds along path 2110b (code silence). Three such ranges are shown in FIG. 3 in blocks 2112, 2114. If significant power is present in each spectral band, a particular audio signal, for example the MIDI code simulating a musical instrument (bassoon for $fl<f<fm$, MIDI code 71, violins for $fm<f<fh$, MIDI code 41, and trumpet for $f>fh$, MIDI code 57) is generated for each spectral band as illustrated, e.g. by blocks 2115, 2116, and 2117. It is understood that other musical instrument sounds can be implemented as piano, piccolo and so on. The loudness, timbre, and attack and decay of each of the sounds is calculated to maximize the differentiation of high spectral components from regular ones to guide the operator in placing the ultrasonic transducer. The MIDI code is a universal code representative of standard musical sounds.

The best "coloring" for the Doppler audio, that is the synthetic audio that provides the most information, will depend upon both the ultrasound system's characteristics (which affect the Doppler spectral characteristics) and the Doppler signal that is to be optimally detected (e.g. valve leakage rather than stenosis); therefore, the particular coloring of the Doppler audio should be designed for both of these factors, as well as who will be listening (experience, hearing levels, etc).

Figure 4:
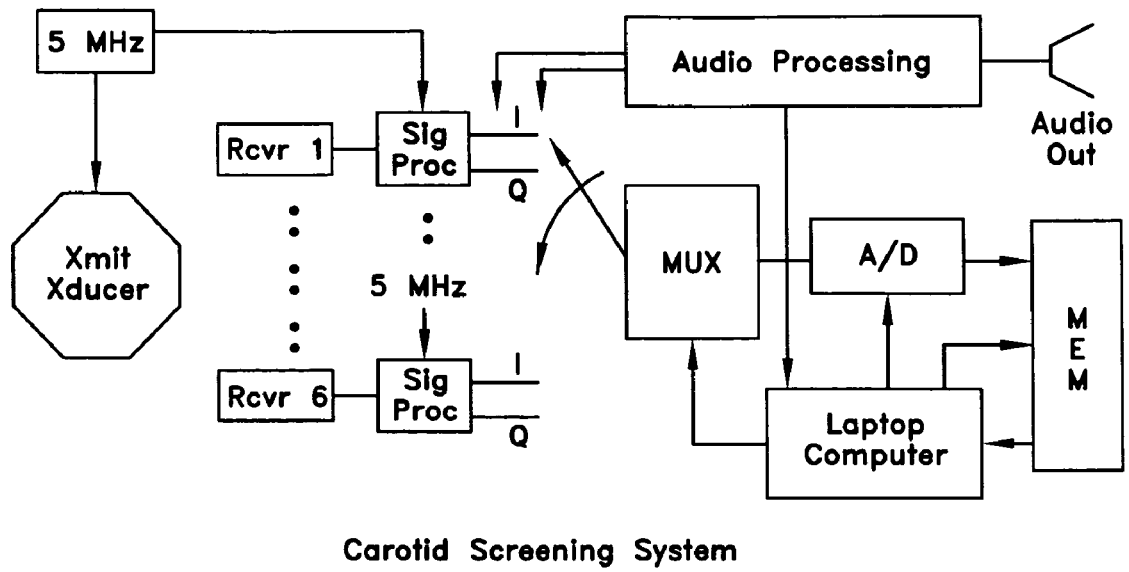
FIG. 4 shows a schematic representation of a conventional carotid screening Doppler system.

FIG. 4 shows the signal processing for the carotid screening system previously referenced. In this system, the operator moves the probe over the carotid arteries to find a spot that is suspicious for stenosis, guided by the audio derived from the Doppler signals. In the previous system, these Doppler signals were derived in the usual way, (i.e. as in FIG. 1). The A/D converter circuit and (laptop) computer shown in FIG. 4 are only used to determine the velocity of blood once a suspicious area is found using the guidance of the analog-generated audio signal.

Figure 5:
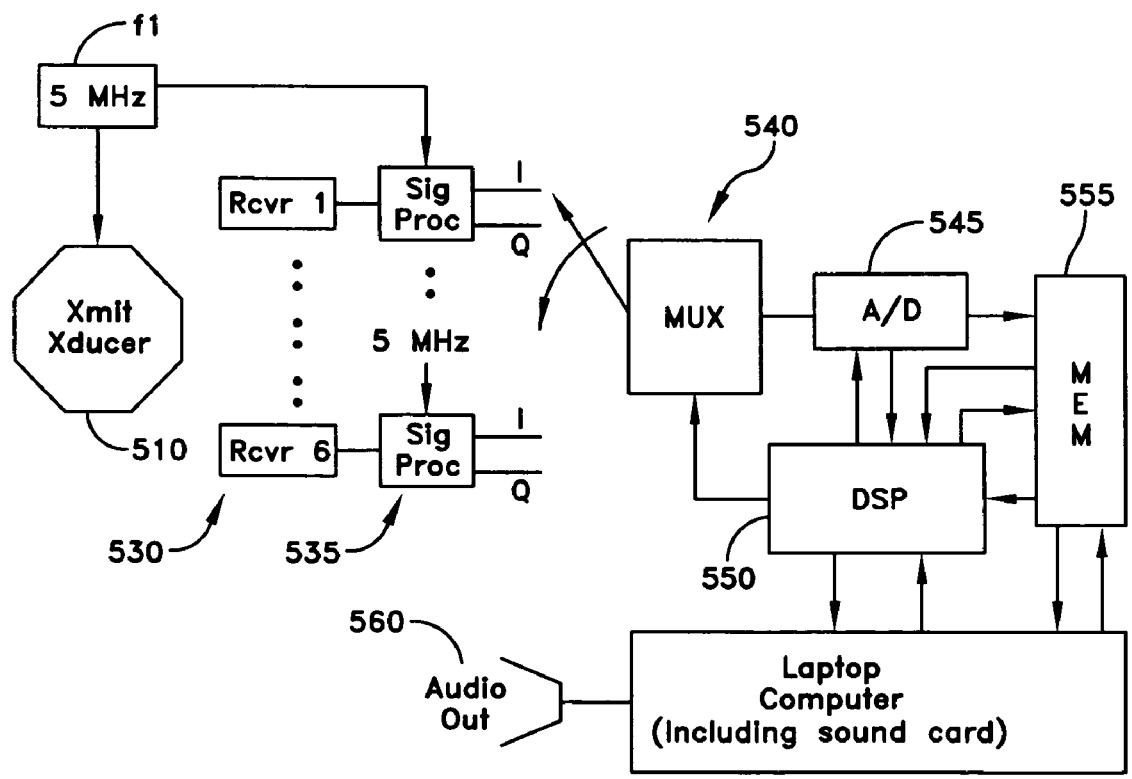
FIG. 5 is a schematic representation of the electronics used in a carotid screening system that generates synthesized Doppler audio.

FIG. 5 shows an exemplary embodiment of an apparatus according to an aspect of the invention for SDA. The system incorporates a digital signal-processing (DSP) unit 550 adapted to calculate power spectra quickly, e.g. 512-point complex array to power spectrum in about 800 microseconds, or 64-point spectra in 70 microseconds. For example, one such device suitable for use with the present invention is an Analog Devices "Shark DSP" processor and memory (such DSP modules are known to those skilled in the art). This "FFT engine" can be used to calculate the high resolution spectra used for the exact velocity calculation and normal-abnormal decision, previously performed in portable (e.g. laptop) computer as described in the referenced carotid screening system, but much faster. Here, it is further utilized to generate low-resolution spectra at a high rate to generate SDA. For example, using the 20 KHz sampling rate as presently used in the carotid instrument, a new 64 point array would be gathered in about 3.20 milliseconds. Overlapping the data by 50% for increased updating, 1.6 millisecond to update the audio would provide real time audio. The FFT engine will generate 6 power spectra from these arrays in 6×70 microseconds, or 420 microseconds, much less than the acquisition time of the data, so providing real-time capability. The DSP further calculates sound tone(s) as described in FIGS. 2 and 3 and adds the sound tone(s) to the received Doppler signal information contained in the calculated spectra. The combined data is converted to analog signals by well-known Digital-to-Analog techniques which are generally contained in the laptop computer (e.g. needed to play CD's or MP3's) so as to produce the synthetic output audio signal 560.

In operation, the system of FIG. 5 functions as follows: The operator moves scanning instrument 700 (FIG. 7) scanhead 710 containing each of the six receiving transducers 530 (FIG. 5) over the surface of a patient's skin, and in a particular application, over the carotid artery. The scanning instrument is moved until the operator hears, e.g. the loudest trumpet sounds, which, according to FIG. 3, would correspond to where the blood is moving most swiftly. The operator would then press a button 720 on the neck of scanhead 710 in order to cause a time segment of the acoustic data to be received and processed by the system. After several seconds (for example 3 seconds), the signal data output from the six receiver transducers 530 (identified as 1 . . . 6) would be multiplexed (block 540) digitized (block 545) and recorded in memory unit 555 (e.g. RAM, ROM) shown in FIG. 5. The data would then be FFT analyzed by DSP 550, which is set to calculate high resolution spectra, and the absolute velocity determined using well known vector Doppler techniques, such as those described in "Easy-to-Use Blood Velocity Measurement Instruments", Vilkomerson D, and Chilipka T, Proceedings of Medical Imaging 2003, W. Walker and M Insana Eds., Proceedings of SPIE, Volume 5035; SPIE, Bellingham, Wash. 2003. The calculated absolute velocity is displayed to the operator via the computer laptop display, so as to enable the operator to determine whether the stenosis is dangerous (e.g. absolute velocity greater than 125 cm/sec), and from this determination, whether to send the patient for further studies.

From the above, it is understood that the output audio signal 560 represents a "stained" Doppler Signal, wherein the artificially generated signal (or synthesized signal) is combined, added or superimposed on the conventionally generated Doppler Signal so as to provide the output audio signal 560. It is further understood that the synthesized audio signal can be added or superimposed on the converted Doppler Signal in any desired ratio, thereby enabling the user to control the amount of synthetic or natural signal.

Figure 6:
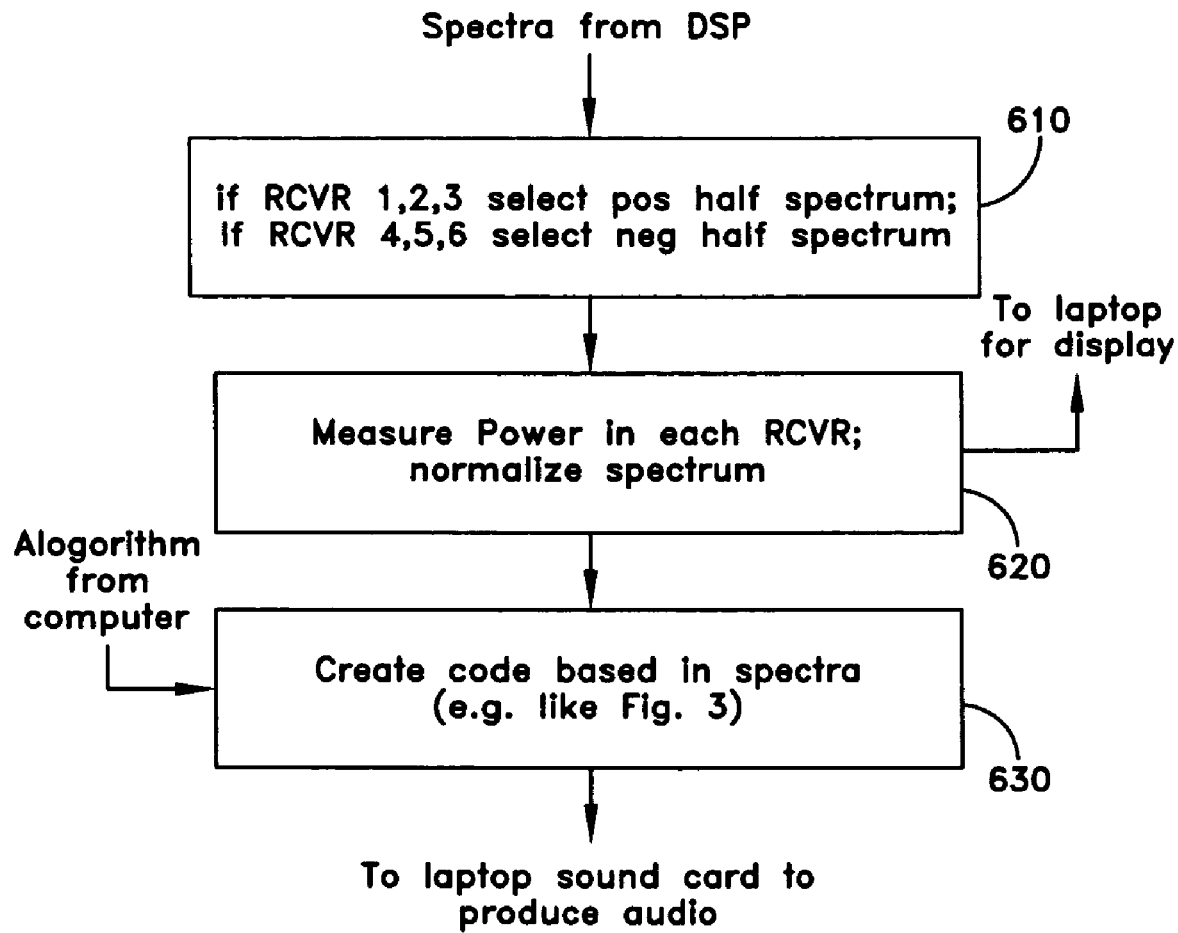
FIG. 6 indicates the processing of the power spectra to produce the synthesized Doppler audio for the instrument of FIG. 5.

FIG. 6 is a simplified flow-chart illustrating how the stream of power spectra produced by the FFT engine are used to generate the SDA. The first step is to ensure that the Doppler signals are from the carotid artery, rather than due to the jugular vein, which often overlies the carotid artery. As discussed in the referenced article, the scanhead of the carotid screening system is placed over the vessels oriented on the neck so that three of the receivers are always toward the head (say those numbered 1,2,3) and three toward the body (4,5,6); therefore, blood flowing in the carotid toward the head will produce positive Doppler shifts in receivers 1,2,3 and negative Doppler shifts in receivers 4,5,6 (block 610). The jugular vein carries blood away from the head; it will produce negative shifts in receivers 1,2,3 and positive shifts in 4,5,6. Therefore, using only the positive parts of the spectra from receivers 1,2,3, and the negative parts of 4,5,6 can eliminate any signal from the jugular vein; using the positive parts of the spectra from receivers 1,2,3 and the negative halves of the spectra 4,5,6 ensures that the Doppler signals generated are from the carotid.

After the carotid signals have been selected from the total Doppler signal, the relative power in each receiver is calculated (block 620) by summing the bins; this information on relative power is displayed to help the operator keep the probe centered over the vessel as well as allowing the gain of each receiver to be automatically adjusted.

Finally, an algorithm, e.g. like the one shown in FIG. 3, is used to determine the distribution of energy, i.e. in high frequencies and low frequencies, from all the receivers (block 630). This information, along with the total energy, is used to produce the code for synthetic audio that emphasizes the signals that may indicate dangerous stenoses, ensuring that the operator perceives the proper positioning to detect dangerous stenoses. (It is assumed that the computer contains the appropriate "sound card" that translates digital codes into audio; if necessary, the computer should be purchased with such a sound card for generating the synthetic audio.)

The use of synthetic Doppler audio may increase the usefulness of Doppler instruments by helping operators find the diseased portions of the circulatory system.

It should be noted that the algorithm to generate the synthetic audio may also utilize time information: for example, it is known that stenoses cause turbulence in the flow shortly after systole, so noting changes in the relative Doppler power among the receivers can show turbulence, and synthetic Doppler audio can incorporate this information into the waveform.

Other aspects of the signal can be incorporated into the coding of the synthesized Doppler audio to maximize the usefulness of the Doppler examination.

In regard to the above discussion one utilizes the Fast Fourier Transform which basically is a method of characterizing the spectrum of finite, discrete sequences obtained by sampling continuous signals. The computer algorithm know as the Fast Fourier Transform (FFT) that implements the discrete Fourier Transform (DFT) is suited for either software or hardware implementation. Based on the sampling period, a continuous time signal f(t) with a Fourier Transform (F(w)) is sampled at constant intervals (T), with a sampling period T and sampling frequency $w_s$ which is inversely proportional to T. One therefore obtains a spectrum of the sampled signal. The sampling operation produces a spectrum composed of copies of the Fourier Transform (F(w)) shifted by integer multiples of the sampling frequency. A consequence of this property is the sampling theorem. This states that if a continuous time signal is band limited than it can be reconstructed form its samples. The use of the Fast Fourier Transform is widely employed in speech recognition and speech processing signals as well as the calculation and analysis of power levels for each of speech frequencies of concern. The method of obtaining the power level of the Doppler signals as generated by an ultrasound system is easily understood by one skilled in the art. Once the power levels of each spectral component are determined then one basically converts predetermined power levels into distinct associated audio signals. This enables the user of the ultrasonic system to audibly respond to the different tones or different musical sounds to enable one to determine the nature of the fluid flow and therefore to indicate or respond to the detection of a certain condition manifested in a moving fluid. As indicated above, the moving fluid discussed is body fluid such as blood which contains red platelets which move with predetermined velocities. In this manner an impinging ultrasonic wave will produce Doppler signals based on the movement of the fluid and these Doppler signals are analyzed to produce spectral data indicative of the velocity. This spectral data is analyzed and one can therefore obtain a power spectrum indicative of fluid velocity and within given frequency ranges. The audio synthesizer or other device then generates an audio signal indicative of that range.

Thus, as one can ascertain there are many alternate methods and embodiments which will be discerned by one skilled in the art, all of which are encompassed within the spirit and scope of claims appended hereto.

What is claimed is:

1. Apparatus for generating selected audio signals to aid in the detection of a certain condition of a moving fluid, comprising:
   an ultrasound system for measuring the velocity of a fluid and operative to provide spectral data indicative of said velocity,
   a processor responsive to said spectral data and operative to analyze at least one power spectrum indicative of a fluid velocity in a given range to provide an output signal associated with said range, and
   a generator responsive to said output signal to provide a unique audio signal according to said given range, wherein said unique audio signal comprises a superposition of an audio signal associated with known characteristics corresponding to said range onto a signal associated with said fluid velocity.

2. The apparatus according to claim 1, wherein said processor is operative to analyze a said at least one power spectrum and to provide an output signal for each of a plurality of ranges within said analyzed-spectrum and said generator responsive to said output signals to provide a unique audio signal having predetermined characteristics for each range to enable a user to distinguish said audible signals associated with each range.

3. The apparatus according to claim 1, wherein said ultrasound system provides quadrature components of the Doppler frequencies according to the velocity of said fluid.

4. The apparatus according to claim 1, wherein said moving fluid is a body fluid such as blood and said certain condition is stenosis.

5. The apparatus according to claim 1, wherein said processor is a digital computer responsive to spectral data to analyze a Fast Fourier Transform (FFT) spectrum to provide, at an output, a sequence of digital numbers representing a power at different Doppler frequencies.

6. The apparatus according to claim 2, wherein each audible signal simulates a different musical instrument.

7. The apparatus according to claim 3, wherein said processor analyzes the level of signal power of generated Doppler frequencies.

8. The apparatus according to claim 7, wherein said processor provides output signals when said level of signal power exceeds a predetermined value.

9. The apparatus according to claim 5, wherein said digital computer provides digital output signals for power levels exceeding a predetermined value.

10. A method for generating elected audio signals to aid in the detection of certain conditions, comprising the steps of:
    generating an ultrasonic signal,
    causing said signal to impinge upon a moving fluid to provide Doppler spectral data according to the velocity of said fluid,
    analyzing the spectral data to determine the level of power at different Doppler frequency ranges in the said spectral data,
    producing a unique audio signal for each Doppler frequency range to enable an operator to respond to said unique audio signal to determine a certain condition, wherein said unique audio signal comprises a superposition of an audio signal associated with known characteristics corresponding to said ranges to a signal associated with said fluid velocity.

11. The method according to claim 10, wherein said moving fluid is blood and said certain condition is a carotid disease.

12. The method according to claim 10, wherein said audio signal simulates a musical instrument with a different musical instrument having said known characteristics simulated for each Doppler frequency range.

13. The method according to claim 10, wherein said ultrasonic signal is caused to impinge upon the carotid artery.

14. The method according to claim 10, wherein the step of analyzing includes analyzing the FFT spectrum to produce a sequence digital numbers representing the power at different Doppler frequencies.

15. The method according to claim 10 further including employing an audio synthesizer to produce said unique audio signal.

16. The method according to claim 10, wherein said Doppler frequency range are more than 2 ranges.

17. The method according to claim 11, wherein the style of analyzing includes noting changes in Doppler power indicative of turbulence due to stenosis and producing audio signal changes according to said turbulence.

18. The method according to claim 12 further including the step of determining the power level at said different Doppler frequencies and providing an output signal when a predetermined level is exceeded.

19. The method according to claim 12, wherein said musical instruments are selected from a bassoon, violin and trumpet.

20. The method according to claim 14, wherein said analysis of said FFT spectrum is supplemented by providing a digital signal processor (DSP) to calculate high resolution spectra.

* * * * *

UNITED STATES PATENT AND TRADEMARK OFFICE
CERTIFICATE OF CORRECTION

PATENT NO. : 7,713,207 B2 Page 1 of 1
APPLICATION NO. : 11/593887
DATED : May 11, 2010
INVENTOR(S) : David Vilkomerson It is certified that error appears in the above-identified patent and that said Letters Patent is hereby corrected as shown below:

In Column 1, line 12, insert the following:

--Government Interests

FEDERALLY SPONSORED RESEARCH OR DEVELOPMENT
This invention was made with government support under Grant R44 HL072534 awarded by NHLBI/NIH. The Government has certain rights in this invention.--

Signed and Sealed this

Twentieth Day of July, 2010

David J. Kappos
*Director of the United States Patent and Trademark Office*